United States Patent [19]

Upham

[11] Patent Number: 5,628,330

[45] Date of Patent: May 13, 1997

[54] APPARATUS FOR TREATING PEOPLE AFFLICTED WITH TINNITUS

[76] Inventor: George W. Upham, 2 Williams Rd., Lynnfield, Mass. 01940

[21] Appl. No.: 404,596

[22] Filed: Mar. 15, 1995

[51] Int. Cl.$^6$ .................................................. A61F 11/00
[52] U.S. Cl. .................................................. 128/864; 128/867
[58] Field of Search .................................. 128/846, 858, 128/859–866

[56] References Cited

U.S. PATENT DOCUMENTS

| | | | |
|---|---|---|---|
| 993,620 | 5/1911 | Quinn | 128/866 |
| 1,312,493 | 8/1919 | Thesis | 128/866 |
| 1,873,864 | 8/1932 | Ely | 128/866 |
| 2,684,067 | 7/1954 | Lienard | 128/866 |
| 2,858,544 | 11/1958 | Roth | 128/866 |
| 3,408,658 | 11/1968 | Beguin | 128/866 |
| 4,408,605 | 10/1983 | Doerr | 128/864 |

*Primary Examiner*—Michael A. Brown
*Attorney, Agent, or Firm*—Robert T. Dunn, Esq.

[57] ABSTRACT

Methods and means of treating a person afflicted with Tinnitus in order to relieve the discomfort and aggravation of the affliction uses apparatus that includes: a metal shell of generally hemispherical shape and diameter about the same as a person's head, nested in a similarly shaped larger shell, the space between the nested shells being filled with a natural, soft, flexible, thermally insulating material that may be animal or plant, the two shells being figures of revolution about a common axis and attached together along the common axis with the material in between, compressed somewhat by the attachment, and a handle, whereby the afflicted person can hold the apparatus against his afflicted ear for repeated intervals to relief is noted by the user after several days of these treatments in order to relieve the discomfort and aggravation of the affliction.

18 Claims, 6 Drawing Sheets

APPARATUS FOR TREATING PEOPLE AFFLICTED WITH TINNITUS

BACKGROUND OF THE INVENTION

This invention relates to apparatus for treating a person afflicted with Tinnitus in order to relieve the discomfort and aggravation of the affliction.

Tinnitus is the sound one hears when there is no external cause for that sound. The most common description of tinnitus is "ringing", but sounds such as roaring, hissing, whistling, music, steam, and numerous others have been reported by those afflicted with tinnitus.

Subjective tinnitus is heard only by the person afflicted. It is very common, about 20% of the population are beset at some time in their life. About 5% of the population suffers from severe chronic tinnitus that may require medical management. Some medical authorities claim that tinnitus is due either to Meniere's disease or to hardening of the arteries in and around the ear. However, in general, the medical community says that tinnitus is not a disease There are many causes of tinnitus. The most frequent cause recognized by all authorities is exposure to loud sounds. Tinnitus-like symptoms are associated with just about every thing which can go wrong in the human auditory system. If arteriosclerosis produces obstructions to blood flow in vessels near the ear, a special form of tinnitus-like otoacoustic emissions, called pulsatile emissions (also improperly called pulsatile tinnitus), may result. Pulsatile emissions are a noise in the ear that is synchronous with the heart beat. People with pulsatile should probably see a cardiovascular specialist. Pulsatile tinnitus has been treated with some success with Masking techniques (described hereinbelow).

It is sometimes found when the otoacoustic emissions are pulsatile, that pressure on the jaw will stop them. Furthermore, these emissions can, in some cases, be masked by using a low-pitched noise, such as the sound of a waterfall with a tone control on full bass. Because pressure on the jaw has relieved these tinnitus-like pulsatile emissions, some who are so afflicted have been advised to consult their dentist.

One theory of the cause of most tinnitus is that the inner ear hairs are altered by the aging process, somewhat the way hair on the head is altered with aging by turning gray, thinning and falling out. Generally tinnitus comes within the field of otoacoustic emissions. Recent studies in the field of otoacoustic emissions suggest that the emissions are due to movement of the hair cells in the inner ear. More particularly, it is movement of the cilia on the cuticular plate of the hair cells in the inner ear. These cilia are very different from external hair; they do not turn gray or fall out like hair on the head. The aging process, however, is a very real phenomenon that involves the inner ear cilia and hair cells, but it is not simply that the ear gets older as the cause of tinnitus, rather it is an accumulation of noise damage over time. Many who are afflicted with tinnitus report that it came on suddenly.

It should be clear that all otoacoustic emissions are not tinnitus. Some investigators had hoped that all otoacoustic emissions would turn out to be tinnitus and so the identification of tinnitus could be easily and reliably established. That is not the case.

Another aggravating effect of tinnitus is the hearing loss that accompanies the tinnitus emissions as background noise. The only thing that can be done about this hearing loss, so long as the emissions persist, is to try a properly fit hearing aid.

Famous people who have experienced the phantom sounds of tinnitus include the great 19th-century naturalist Charles Darwin, the father of evolutionary theory. Other notables are Beethoven, Luther, and Van Gogh. It is reported that Darwin's kept a careful record of the rise and fall of the tinnitus noises in an attempt to discover what caused his "bad days". Darwin's scientific accomplishments included important work in early child hood development as well as botany, geology and zoology. These examples show that tinnitus is common and, as uncomfortable and aggravating as it is, it is still possible to use one's strength of will and love of life to overcome the suffering and go on to a very productive life. Another sufferer of today is President Reagan who became afflicted with tinnitus from the noise of gunshot during filming of moving pictures in his youth.

Currently common advice to those concerned about Tinnitus include the following:

(a) Avoid loud sounds whenever possible; even lawnmowers, radio headsets, and vacuum cleaners are potential dangers, so use ear protection such as ear plugs or ear muffs when exposed to these sounds.

(b) Don't fly in airplanes when you have a cold and, if you must fly, use decongestants and/or nosedrops to keep ear passages clear and so minimize the chances for ear damage.

(c) See a doctor immediately if you suddenly experience problems with hearing, dizziness or head noises.

(d) Consult your doctor about possible side effects involving hearing before you take new medications.

Current Techniques of Treating Tinnitus

Masking the tinnitus sound has been the birth of modern treatment for tinnitus. Many of those afflicted report that the tinnitus emissions are not noticeable when masked by the sound of falling water. Hearing-aid manufacturers have picked up on this effect and now provide an external sound source (built into the hearing aid) that the wearer accepts as more pleasant than the internal tinnitus noise. Now, thousands of tinnitus sufferers have embraced masking in this and other its forms as a method for managing their tinnitus.

Clearly, Masking is a non-invasive, non-chemical technique of developing a program, particularly with volume control, to reduce the discomfort and aggravation of the tinnitus noise. Masking is often combined with a tension reducing regime of relaxation during waking hours and Masking is used even during sleep.

Another non-invasive, non-chemical technique that has been used with some success during waking hours is Biofeedback. Feedback therapy has been orchestrated to reduce stress both in the facial muscles, particularly about the temporomandibular or jaw joint (TMJ) and the internal "fight or flight" emergency response of the sympathetic nervous system. Biofeedback muscle treatment has been effected through placement of sensors on the skin, not unlike the electrocardiograph (EKG) attachments, which signal the subject's level of electrical muscular tension and is displayed on an electronic monitor with sound and color. Also, changes over the involuntary sympathetic nervous system are detected as the temperature at a finger tip (cold clammy hands are often a sign of high level anxiety and stress, while warm hands show inner repose). In Biofeedback, the subject observes the monitor or the display of the detected biological parameter and makes conscious effort to make the parameter normal or ideal. For those afflicted with tinnitus who use both Masking and Biofeedback techniques, using both during waking hours and Masking while sleeping, it often takes several months before they report that they are doing well (significant relieve of the tinnitus aggravation) and thereafter, they must repeat the Masking technique often, at least while sleeping, in order to be able to report that they are still doing well.

SUMMARY OF THE INVENTION

Thus, the most successful present technique for treating tinnitus is the combination of Masking and Biofeedback for months, followed by frequent Masking, at least while sleeping.

It is another object of the present invention to provide a method and means of treating a person afflicted with tinnitus to relieve the discomfort and aggravation thereof.

It is another object of the present invention to provide a method and means of treating a person afflicted with tinnitus to relieve the discomfort and aggravation thereof, which is non-invasive and non-chemical.

It is another object of the present invention to provide a method and means of treating a person afflicted with tinnitus to relieve the discomfort and aggravation thereof, which requires only periodic use to maintain the relief.

It is another object of the present invention to provide a method and means of treating a person afflicted with tinnitus to relieve the discomfort and aggravation thereof, which can be self administered.

It is another object of the present invention to provide a method and means of treating a person afflicted with tinnitus to relieve the discomfort and aggravation thereof, which makes use of the natural healing processes of the human body.

According to the present invention, apparatus that includes a metal shell of generally hemispherical shape and diameter about the same as a person's head is nested in a similarly shaped larger shell, the space between the nested shells being filled with a natural, soft, flexible, thermally insulating material that may be comprised of: fibrous animal or vegetable material including animal wool of various kinds and cotton, woven or unwoven; or non-fibrous material like soft rubber. The two metal shells are figures of revolution about a common axis and are attached together along the common axis with the natural, soft, flexible, thermally insulating material in between compressed somewhat by the attachment. The attachment extends along the axis beyond the outer shell and is provided with a handle. The handle is equipped to be grasped by the user by one hand so that the user can hold the apparatus against his afflicted ear.

Thus, the apparatus is used to bring about relief from tinnitus by grasping the handle and holding the open end thereof lightly against the afflicted ear. Since both ears are usually afflicted with tinnitus at the same time, the preferred treatment is to use two units of the apparatus, one in each hand and hold one against each ear in this fashion. The unit is placed against the ear so that the ear canal is along the unit axis and is held lightly in this position for several minutes (at least 10 to 15 minutes) at a time, every few hours or so during waking hours for several days. Observable relief is noted by the user after several days of these treatments. Thereafter, these treatments need be repeated only twice a day to maintain permanent relief.

This method and apparatus has been discovered by the applicant through trial and error testing on himself and others afflicted with tinnitus, without pursuing any particular scientific or medical theory, except that tinnitus is the result of an injury to the inner ear and that injury must be healed to bring about a relief from the tinnitus emissions. The applicant now believes that the apparatus may focus or somehow direct natural healing processes of the human body to the injured part of the inner ear and/or it may focus or direct external healing energy to the injured part of the ear.

These and other features of the present invention are apparent from the following description of specific embodiments thereof taken in conjunction with the drawings.

DESCRIPTION OF EMBODIMENTS OF THE INVENTION

Figure 1:
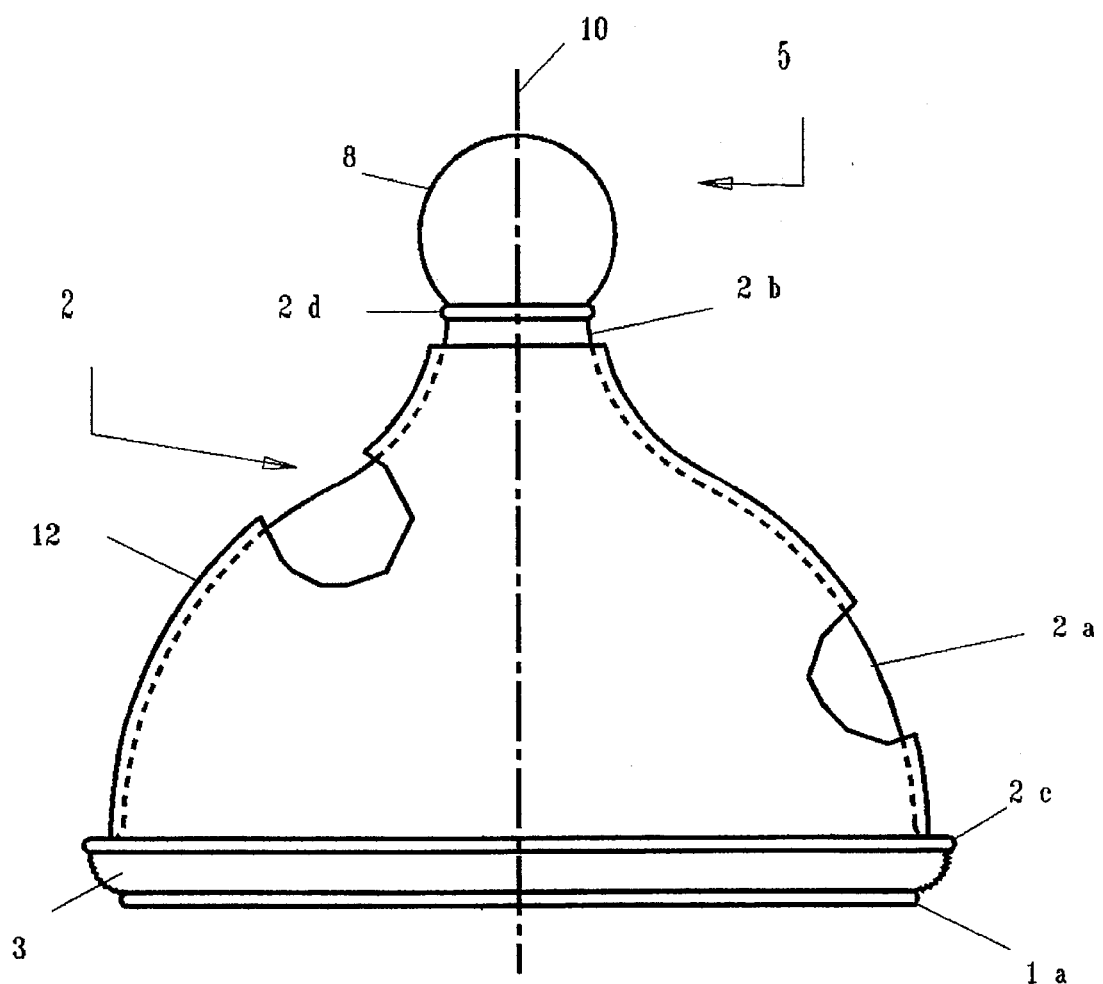
FIG. 1 is an elevation (front) view of the apparatus which is generally a figure of revolution about a common axis shown vertical in this view.
Figure 2:
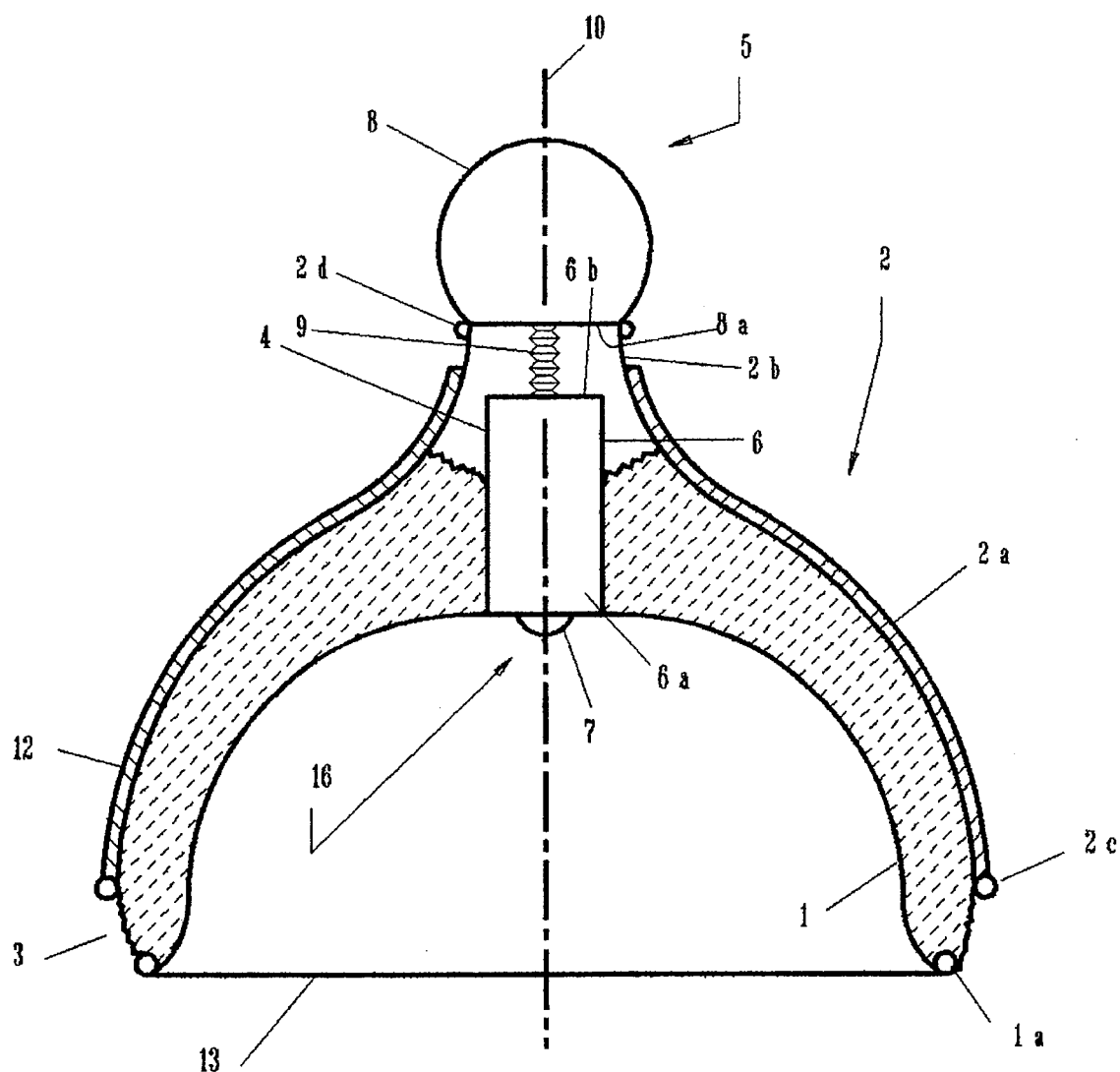
FIG. 2 shows the same elevation view broken away to reveal details of the inside and outside parts thereof.
Figure 3:
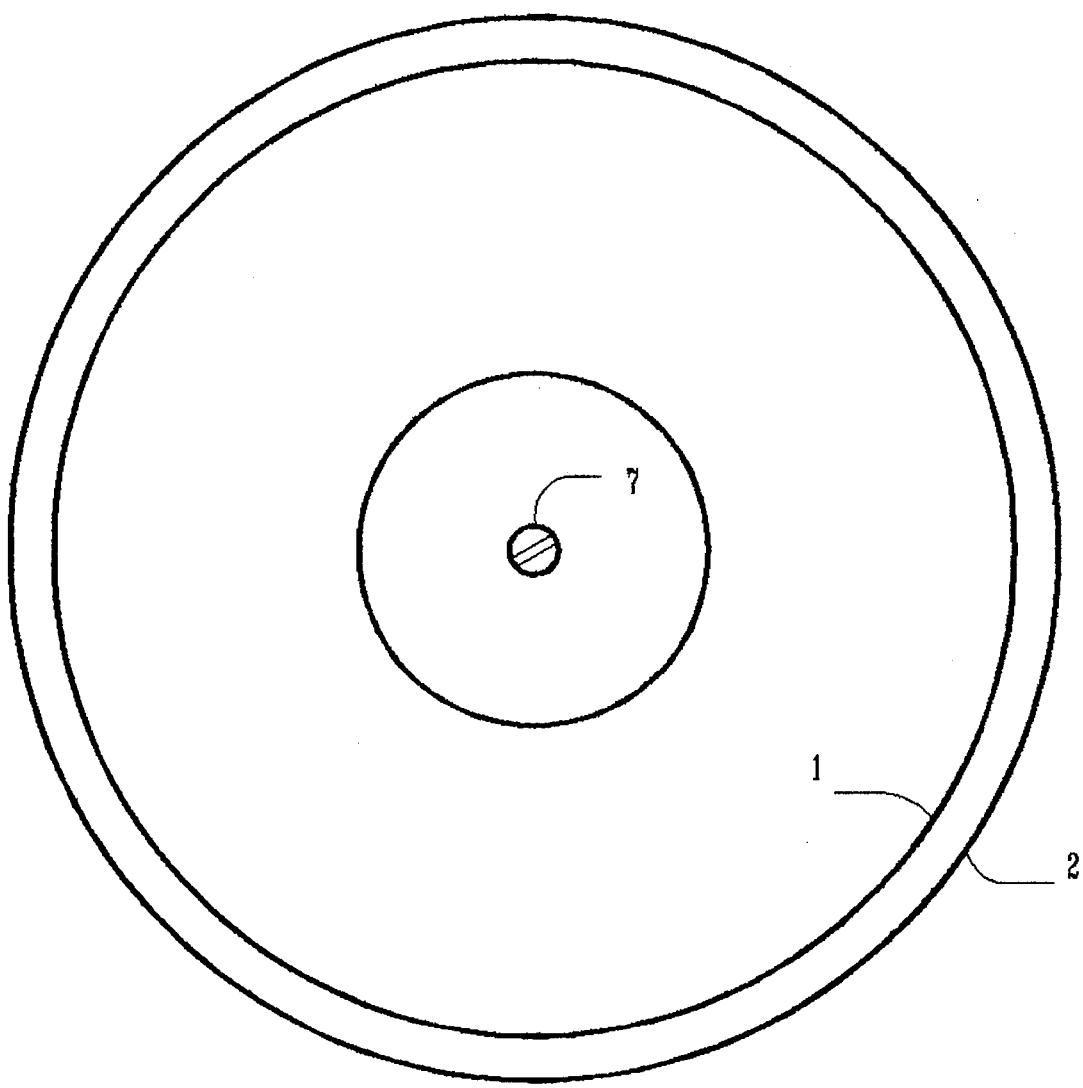
FIG. 3 is a top view of the apparatus.
Figure 4:
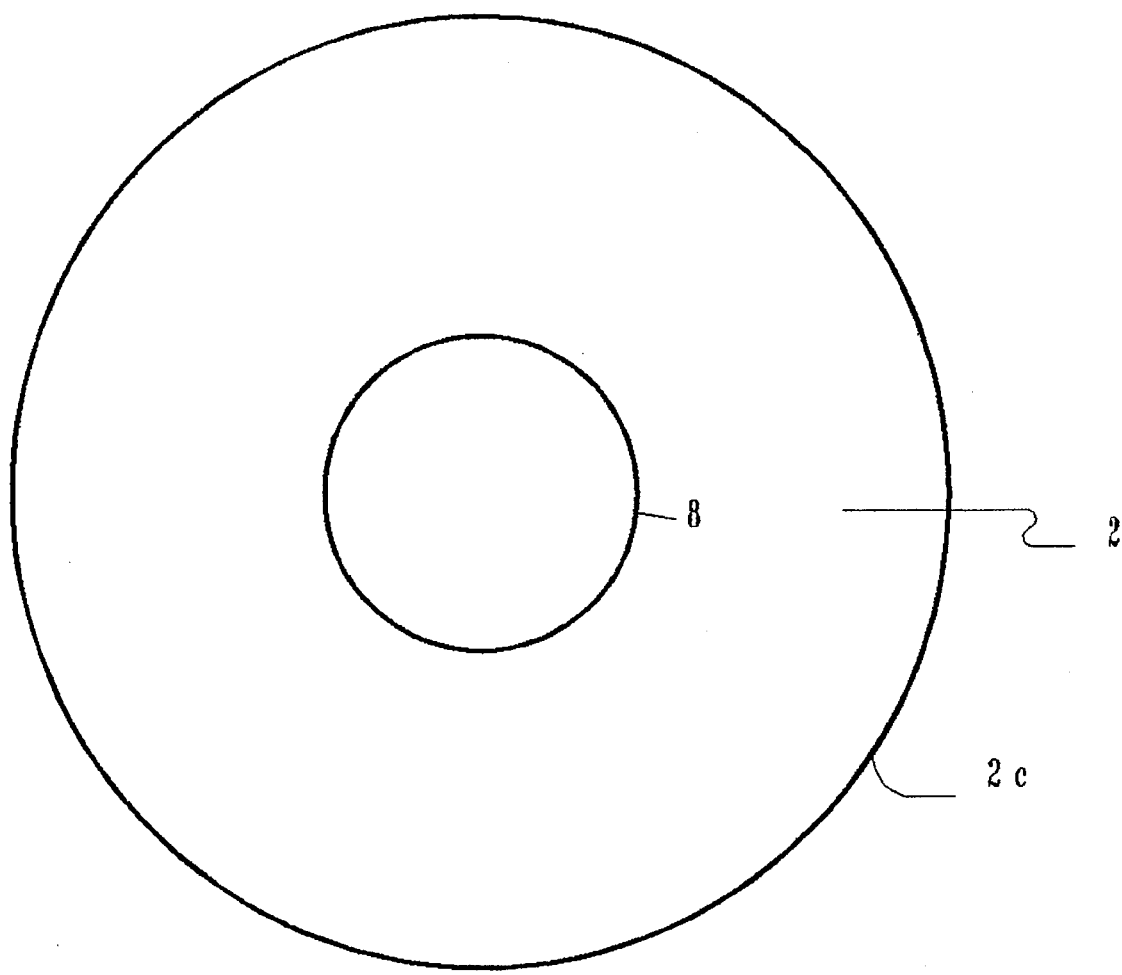
FIG. 4 is a bottom view of the apparatus.
Figure 5:
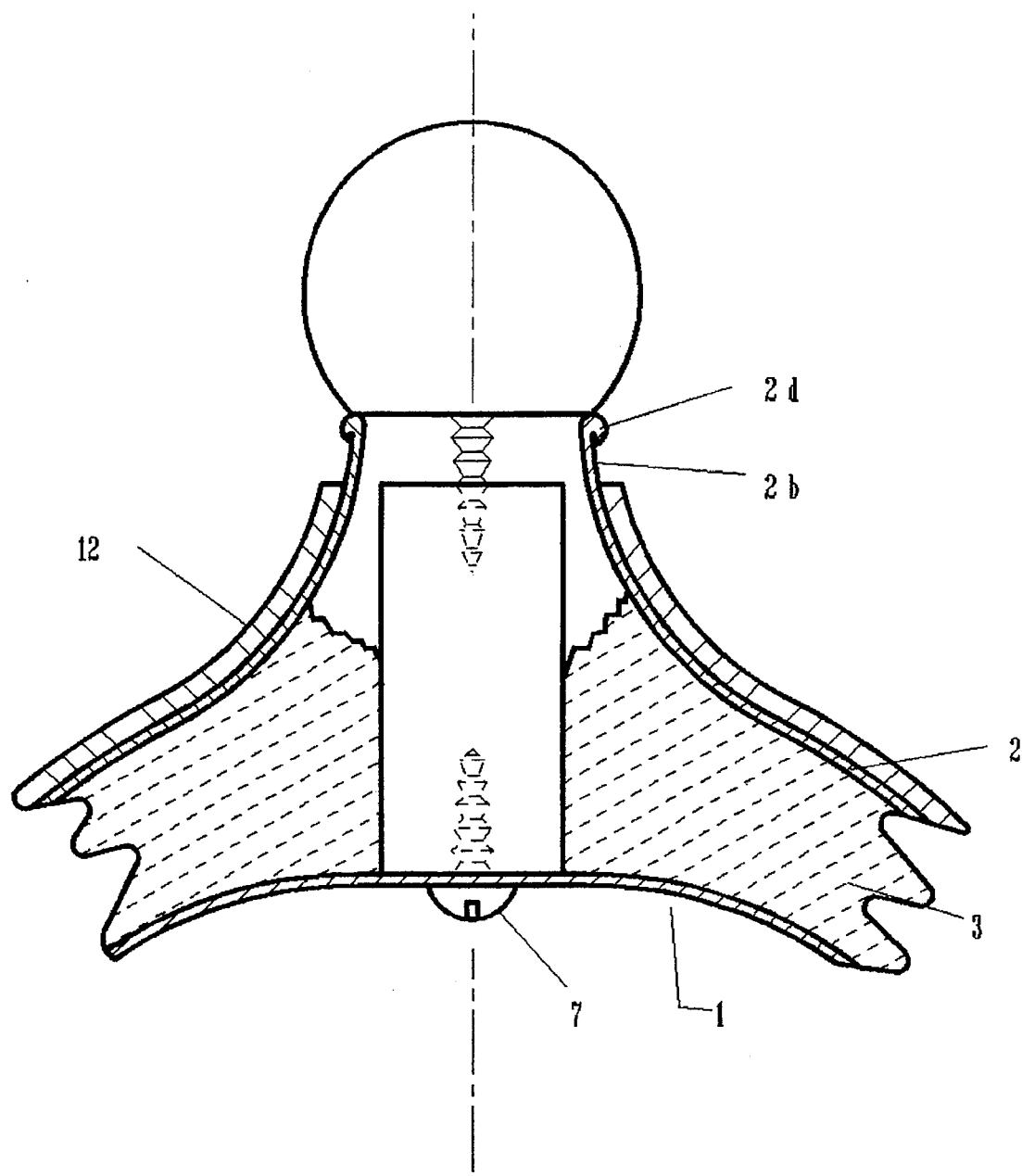
FIG. 5 is an enlarged view of part of FIG. 2.

The apparatus as shown particularly in FIGS. 1 to 5 includes an inner metal shell 1 of generally hemispherical shape and diameter about the same as a person's head, nested in a similarly shaped larger outer shell 2, which are both figures of revolution about common axis 10. The space between the nested shells is filled with a natural, soft, flexible, thermally insulating material 3 that may be comprised of: fibrous animal or vegetable material including animal wool of various kinds and cotton, woven or unwoven; or non-fibrous material like soft rubber. The two metal shells 1 and 2 are figures of revolution about common axis 10 and are attached together along the common axis with the natural, soft, flexible, thermally insulating material 3 in between compressed somewhat by the attachment. The attachment 4 extends along the axis beyond the hemispherical part 2a and within the neck 2b of outer shell 2 and is provided with a handle 5. The handle is equipped to be grasped by the user by one hand so that the user can hold the apparatus against his afflicted ear.

The shells 1 and 2 are made, at least in part of metal and can be made of steel or aluminum sheet metal that is drawn, or otherwise formed, into the shapes shown and then rolled at the edges to strengthen and finish the edges. For example, the shells are drawn from thin sheets of stainless steel and the bare edges are rolled forming a lip for strength and to eliminate sharp edges. Inner shell 1 has rolled edge 1a at the bottom (open) end and outer shell 2, consisting of hemispherical part 2a, in which the inner shell nests, and neck 2b has rolled edge 2c at the bottom and rolled edge 2d at the top at the end of the neck thereof.

The two metal shells 1 and 2 are attached together by attachment 4 in the neck 2b of the outer shell in the space between the shells. This attachment consists on central post 6 concentric with axis 10 attached to inner shell 1 as shown. For that purpose, a clearance hole 1b in shell 1 is provided for attaching screw 7 that securely fastens post 6 to the inner shell. The attachment secures the two shells together by connecting the handle 5, that may consist of ball 8 to the post. For this purpose, ball 8 has affixed thereto an attaching screw 9 that engages a threaded hole in the post.

At assembly, the post is attached to inner shell by screw 7. Then the natural, soft, flexible, thermally insulating material 3 is placed around the inner shell from the rolled edge to and around the post. Then outer shell 2 is placed over the inner shell against material 3 and the two shells are pressed together, bringing the top lip 2d of the outer shell down to just above the top 6b of the post so that the top of the post is a fraction of an inch below the bottom of the handle ball 8. Then the handle ball 8 is placed against top lip 2d so that the screw 9 thereof engages threaded hole 6d in the top of the post. The ball is then screwed onto the assembly drawing the post up into the neck of the outer shell toward the handle ball and compressing material 3 between the shells.

Thereafter, a relatively this outer cover 12 comprised of the same materials as material 3 is attached to the outside of the assembly to complete the apparatus unit and it is ready for use. From time to time, the handle ball 8 may be tightened to maintain material 3 compressed by simply turning the ball screw into the post. The clearance between the top 6b of the post and the bottom 8a of the ball is provided to allow this.

Figure 6:
FIG. 6 illustrates a person holding a unit of the apparatus against each ear according to the method herein of relieving the discomfort and aggravation of tinnitus.

Thus, the apparatus is used to bring about relief from tinnitus as shown in FIG. 6. That figure shows a person 20 who wants relief from tinnitus grasping two units of the apparatus shown in FIGS. 1 to 5, each by the handle and holding the open end thereof lightly against the afflicted ear. Since both ears are usually afflicted with tinnitus at the same time, the preferred treatment is to use two units 21 and 22 of the apparatus, one in each hand and hold one against each ear in this fashion. The unit is placed against the ear so that the ear canal is along the unit axis and is held lightly in this position for several minutes (at least 10 to 15 minutes) at a time, every few hour or so during waking hours for several days. Observable relief is noted by the user after several days of these treatments. Thereafter, these treatments need be repeated only twice a day to maintain permanent relief.

CONCLUSION

While the invention is described herein in connection with preferred embodiments, it will be understood that it is not intended to limit the invention to those embodiment. It is intended to cover all alternatives, modifications, equivalents and variations of those embodiments and their features as may be made by those skilled in the art within the spirit and scope of the invention as defined by the appended claims.

I claim:

1. Apparatus used for relieving a person's discomfort and aggravation of tinnitus comprising, (a) a metal shell of generally hemispherical shape and diameter about the same as said person's head,
   (b) a similarly shaped larger shell around said metal shell, defining a space between said shells
   (c) said space between said shells being filled with several layers of cloth made of natural, soft, flexible, thermally insulating material and
   (d) a handle attached to said apparatus,
   (e) whereby said apparatus may be grasped by the user and held against the user's ear to relieve the discomfort and aggravation of tinnitus.

2. Apparatus as in claim 1 wherein,
   (a) said cloth is made of fibrous animal wool.

3. Apparatus as in claim 2 wherein,
   (a) said fibrous animal wool is woven.

4. Apparatus as in claim 3 wherein,
   (a) said fibrous animal wool is unwoven.

5. Apparatus as in claim 1 wherein,
   (a) said cloth is made of fibrous plant material.

6. Apparatus as in claim 1 wherein,
   (a) said cloth is made of non-fibrous plant material.

7. Apparatus as in claim 6 wherein,
   (a) said non-fibrous plant material is rubber.

8. Apparatus as in claim 1 wherein,
   (a) said similarly shaped larger shell is made of metal.

9. Apparatus as in claim 8 wherein,
   (a) said metal shells are figures of revolution about a common axis with said first mentioned metal shell nested within said larger metal shell and spaced therefrom defining said space therebetween.

10. Apparatus as in claim 9 wherein,
    (a) said metal shells are attached together along said common axis.

11. Apparatus as in claim 10 wherein,
    (a) said metal shells are attached together along said common axis.

12. Apparatus as in claim 11 wherein,
    (a) said metal shells are so attached that said several layers of cloth are in between are compressed somewhat by the attachment.

13. Apparatus as in claim 12 wherein,
    (a) said attachment extends along said axis beyond said larger shell to a handle for holding said apparatus.

14. The method of relieving the discomfort and aggravation of tinnitus in a person afflicted with tinnitus including the steps of:

(a) providing apparatus that is an assembly of a metal shell of generally hemispherical shape and diameter about the same as said person's head, defining the axis of the apparatus, with a similarly shaped larger shell around said metal shell, defining a space between said shells, said space between said shells being filled with several layers of cloth made of a natural, soft, flexible, thermally insulating material and with a handle attached to said apparatus; and
    (b) holding said apparatus against the ear of said person afflicted with tinnitus.

15. The method as in claim 14 wherein,
    (a) said apparatus is held against said ear so that said ear canal is along said apparatus axis and
    (b) said apparatus is held lightly in this position for about 10 to 15 minutes and
    (c) repeating said steps every few hours for several days.

16. The method as in claim 15 whereby,
    (a) said apparatus directs natural healing processes of said person's body to the inner ear.

17. The method as in claim 15 whereby,
    (a) said apparatus directs external healing energy to the injured part of the ear.

18. Apparatus used for relieving a person's discomfort and aggravation of tinnitus comprising:

(a) a metal shell of generally hemispherical shape and diameter about the same as said person's head;
    (b) a similarly shaped larger shell around said metal shell, defining a space between said shells;
    (c) said space between said shells being filled with several layers of cloth made of a natural, soft, flexible, thermally insulating material, selected from any of the following: animal wool, animal wool cloth, fibrous plant material, fibrous plant material cloth and soft rubber; and
    (d) a handle attached to said apparatus;
    (e) whereby said apparatus may be grasped by the user and held against the user's ear to relieve the discomfort and aggravation of tinnitus.

* * * * *